Jan. 3, 1956 E. S. BOERNER Plant Pat. 1,447
ROSE PLANT
Filed Feb. 7, 1955
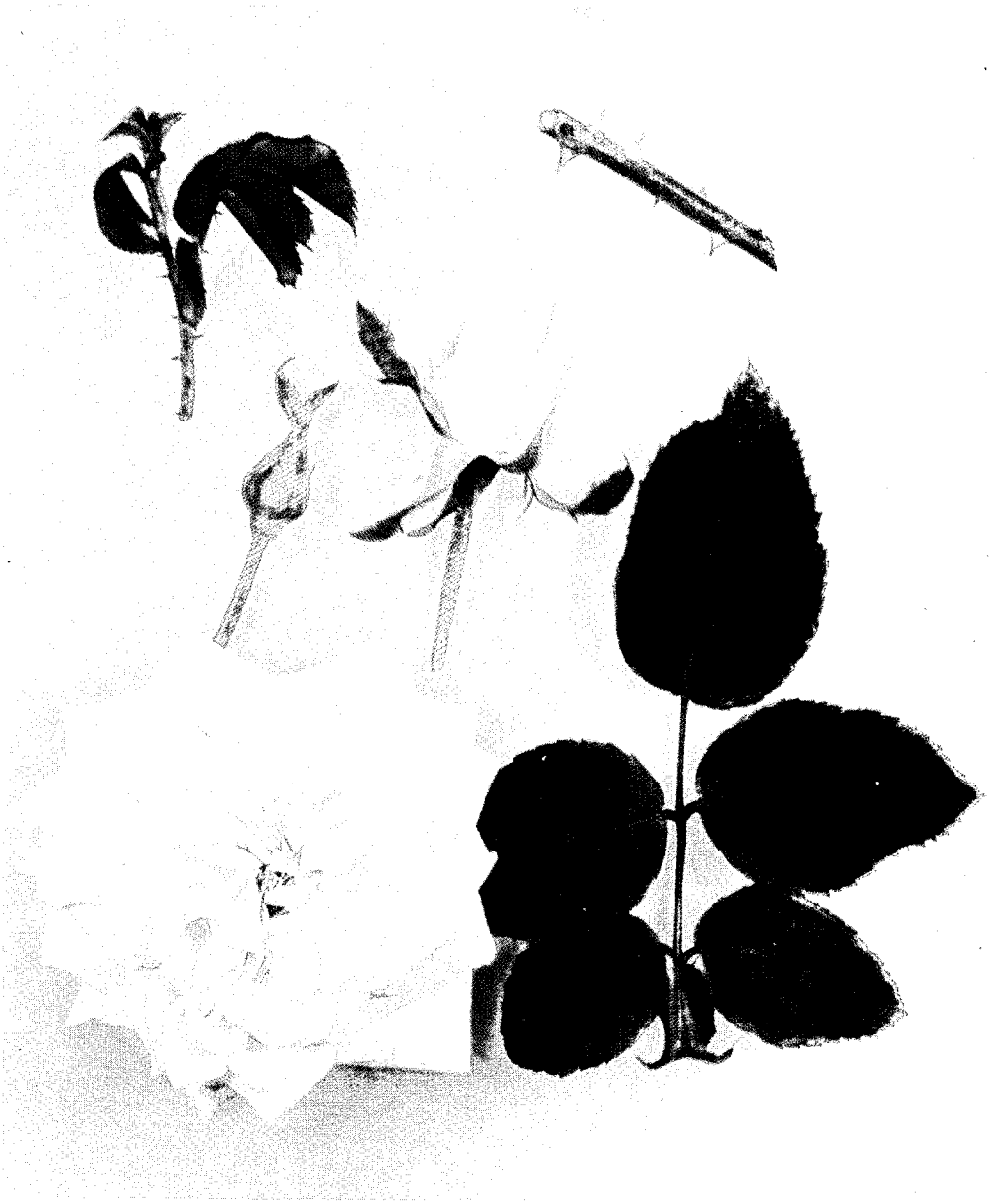
Inventor.
E. S. Boerner
By: Robb & Robb
Attorneys.

United States Patent Office

Plant Pat. 1,447
Patented Jan. 3, 1956

1,447

ROSE PLANT

Eugene S. Boerner, Newark, N. Y., assignor to Jackson & Perkins Company, Newark, N. Y., a corporation of New York Application February 7, 1955, Serial No. 486,748

1 Claim. (Cl. 47—61)

The present invention relates to a new and distinct variety of rose plant of the climber class, which was originated by me by crossing an unnamed and unpatented seedling of the climbing pink rose known as "New Dawn" (Plant Patent No. 1) with the variety "R. M. S. Queen Mary" (Plant Patent No. 249).

The primary objective in making this cross was to produce a new rose variety which retains the everblooming qualities of the variety "New Dawn," but which also intensifies the color of the flowers by virtue of the increased size of the individual flowers which are borne by the new variety. This objective was fully achieved, as evidenced by the following unique combination of characteristics which are outstanding in the new variety:

(1) The large size and superior shape of the flowers;

(2) The everblooming habit and floriferousness comparable to "New Dawn";

(3) The good lasting quality of the flowers when cut and used for cut flowers; and (4) The improved and distinctive color of the flowers which have a general color tonality of La France Pink, lightly overcast with Cartridge Buff.

The foregoing characteristics and distinctions definitely differentiate my new variety from its parents, as well as from all other varieties of this class of which I am aware, and asexual reproduction of the new variety by budding, as performed at Newark, New York, and also at Pleasanton, California, shows that these characteristics and distinctions come true to form and are established and transmitted through succeeding propagations.

The accompanying drawing shows typical specimens of the foliage, stems and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed seedling of the climbing Pink variety "New Dawn."

*Pollen parent.*—"R. M. S. Queen Mary."

Classification:

*Botanic.*—Climber.

*Commercial.*—Climber.

FLOWER (Observations made from specimens grown in a garden at Newark, New York, in the late morning, in the latter part of the month of August.)

Blooming habit: Recurrent—continuous.

Bud:

*Size.*—Large.

*Form.*—Long; pointed; is not affected by wet or hot weather.

*Color.*—When sepals first divide—Begonia Rose, Plate 1. When petals begin to unfurl—Eosine Pink, Plate 1. When half blown: inside of petals—La France Pink, Plate 1, with lower half of the petal lightly overcast with Pale Orange Yellow, Plate 3; reverse of petals—Light Buff, Plate 15, with outer edges of petal La France Pink, Plate 1, and with the lower half of the petal lightly overcast with Empire Yellow, Plate 4.

*Sepals.*—Slightly branched, with "hood" above bud; curl back when petals begin to unfurl. Color: inside—Ouralgreen, Plate 18; outside—Biscay Green, Plate 17.

*Calyx.* — Color — Light Bice Green, Plate 17. Shape—pear. Size—small. Aspect—smooth. Odor when rubbed—none.

*Peduncle.*—Length — medium. Aspect — smooth. Strength—erect; slender. Color—Bice green, Plate 17.

*Opening.*—Opens up well; is not affected by adverse weather conditions.

Bloom:

*Size.*—Very large. Average size when fully expanded—5 inches.

*Borne.*—Singly and several together.

*Stems.*—Medium length; strong.

*Form (when first open).*—High center. Permanence—retains its form to the end, but outer petals curl back slightly.

*Petalage.*—Double (full but open center). Number of petals under normal conditions—from 60 to 65.

*Color.*—Center of flower—Eosine Pink, Plate 1. Outer petals—Ivory Yellow, Plate 30, lightly overcast with La France Pink, Plate 1. Base of petals (aiglet)—Citron Yellow, Plate 16. Inside of petals—La France Pink, Plate 1, lightly overcast with Cartridge Buff, Plate 30. Reverse of petals—Marguerite Yellow, Plate 30, lightly overcast with La France Pink, Plate 1. General tonality from a distance—La France Pink, Plate 1, lightly overcast with Cartridge Buff, Plate 30.

*Discoloration.*—General tonality at end of first day—La France Pink, Plate 1, lightly overcast with Cartridge Buff, Plate 30. Second day—La France Pink, Plate 1, overcast with Cartridge Buff, Plate 30. Third day—La France Pink, Plate 1, overcast with Ivory Yellow, Plate 30.

Petals:

*Texture.*—Leathery; is not affected by wet or hot weather.

*Appearance.*—Inside—satiny; outside—shiny.

*Form.*—Oval.

*Arrangement.*—Informal (with "rags" in center).

*Petaloids in center.*—Few; small.

*Persistence.*—Drop off cleanly.

*Fragrance.*—Moderate. Nature—spicy.

*Lasting quality.*—On the plant—long. As cut flower—long.

GENITAL ORGANS

Stamens, anthers: Medium size; many; mixed with petaloids.

*Color.*—Ochraceous Orange, Plate 15.

Stamens, filaments (threads): Medium length.

*Color.*—Lemon Yellow, Plate 4.

Pollen:

*Color.*—Pale Ochraceous Buff, Plate 15.

Styles: Loosely separated; uneven length; short; thin.

Stigmas:

*Color.*—Martius Yellow, Plate 4.

Ovaries: All enclosed in calyx.

Hips: None.

Seeds: None.

PLANT

Form: Climber.

Growth: Vigorous; upright; branching; attains a height of 10 feet.

Foliage: 5 to 7 leaflets.

*Size.*—Large.

*Quantity.*—Normal.

*Color.*—New foliage: Upper side—Forest Green, Plate 17, lightly overcast with Oxblood Red, Plate 1; under side—Yellowish Olive, Plate 30, overcast with Acajou Red, Plate 13. Old foliage: Upper side—Danube Green, Plate 32, with midrib of Vandyke Red, Plate 13; under side—Jade Green, Plate 31.

*Shape.*—Oval pointed.

*Texture.*—Upper side—leathery; under side—smooth.

*Ribs and veins.*—Ordinary.

*Edge.*—Serrated (saw-toothed).

*Serration.*—Both double and single; small.

*Leaf stem.*—Color—Lincoln Green, Plate 41. Under side—smooth.

*Stipules.*—Medium length; smooth.

Wood:

*New wood.*—Color—Light Cress Green, Plate 31, lightly overcast with Oxblood Red, Plate 1. Bark—smooth.

*Old wood.*—Color—Cress Green, Plate 31. Bark—smooth.

Thorns:

*Thorns.*—Quantity: On main stalks from base—ordinary; on laterals from stalk—ordinary. Form—narrow base; medium length; straight. Color (when young)—Ecru-Olive, Plate 30. Position—irregular.

*Prickles.*—Quantity: On main stalks—none; on laterals—none.

*Short needles.*—Quantity: On main stalks—none; on laterals—none.

I claim:

A new and distinct variety of rose plant of the climber class, substantially as herein shown and described, characterized particularly as to novelty by an everblooming habit and floriferousness comparable to the variety "New Dawn" (Plant Patent No. 1), the large size and superior shape of its flowers, the good lasting quality of its flowers when cut and used for cut flowers, and the improved and distinctive La France Pink, lightly overcast with Cartridge Buff, general color tonality of its flowers.

No references cited.